United States Patent [19]

Carey et al.

[11] Patent Number: 5,332,805

[45] Date of Patent: Jul. 26, 1994

[54] PROCESS FOR THE RECOVERY OF RECOMBINANTLY PRODUCED CHYMOSIN FROM INSOLUBLE AGGREGATE

[75] Inventors: Norman H. Carey, Chinnor; Michael T. Doel, Studley Green; Timothy J. R. Harris, Bracknell; Peter A. Lowe, Reading, all of England

[73] Assignee: Celltech Limited, Berkshire, England

[21] Appl. No.: 677,415

[22] Filed: Mar. 29, 1991

Related U.S. Application Data

[60] Division of Ser. No. 517,414, May 2, 1990, which is a continuation of Ser. No. 147,012, Jan. 15, 1988, abandoned, which is a continuation of Ser. No. 590,589, Feb. 3, 1984, abandoned.

[51] Int. Cl.$^5$ .................. C07K 3/12; C07K 15/06
[52] U.S. Cl. .................. 530/423; 530/300; 530/305; 530/412; 530/422; 435/71.1; 435/71.2; 435/226; 435/252.3; 435/252.33
[58] Field of Search .................. 435/71.1, 226, 252.3, 435/71.2, 183, 252.33; 530/300, 305, 412, 422, 423

[56] References Cited

U.S. PATENT DOCUMENTS

| | | | |
|---|---|---|---|
| 4,136,201 | 1/1979 | Feldman | 435/226 |
| 4,512,922 | 4/1985 | Jones et al. | 435/69.1 |
| 4,526,868 | 7/1985 | Shasuzzaman et al. | 435/226 |
| 4,656,255 | 4/1987 | Seely | 530/412 |
| 4,721,673 | 1/1988 | Uren et al. | 435/183 |
| 4,831,120 | 5/1989 | Aviv et al. | 530/399 |
| 4,935,354 | 6/1990 | Hayenga et al. | 435/69.1 |
| 4,975,529 | 12/1990 | Frazier et al. | 530/399 |
| 4,997,916 | 3/1991 | Aviv et al. | 530/399 |
| 5,064,943 | 11/1991 | McCoy et al. | 530/399 |

OTHER PUBLICATIONS

Zgirski et al., "Lability of Human and Porcine Coeruloplasmins in Alkaline Medium", Acta Biochimica Polonica, vol. 30, No. 1, pp. 33-38 (1983).
Bennett, (1967), Methods in Enzymology, vol. XI, pp. 211-212.
Ainsworth, (1977), Steady-State Enzymes Kinetics, p. 3.
Jensen et al., (1982), Biochima et Biophys, vol. 705, 249-256.
McPhie, (1980), J. Biol. Chem., vol. 255, pp. 4048-4052.
Nishimori et al., (1982), Gene, vol. 19, pp. 337-344.
Wetzel et al., (1981), Gene, vol. 16, pp. 63-71.

Primary Examiner—Richard A. Schwartz
Assistant Examiner—J. Le Guyader
Attorney, Agent, or Firm—Woodcock Washburn Kurtz Mackiewicz & Norris

[57] ABSTRACT

The production of recombinant chymosin is disclosed in which an insoluble form of chymosin precursor is produced by a bacterial host cell transformed by a vector including a coding sequence for said precursor. Solubilization of said insoluble form of chymosin precursor is accomplished using urea at a concentration of at least 7M or guanidine hydrochloride at a concentration of at least 6M prior to cleaving said precursor to form chymosin. Said solubilization preferably additionally involves the denaturation of said precursor in an alkaline aqueous solution, e.g., at a pH between a 9 and 11.5

10 Claims, No Drawings

PROCESS FOR THE RECOVERY OF RECOMBINANTLY PRODUCED CHYMOSIN FROM INSOLUBLE AGGREGATE

This is a division of application Ser. No. 07/517,414, filed May 2, 1990 which is a continuation of Ser. No. 07/147,012, filed Jan. 15, 1988, now abandoned, which was a FWC of Ser. No. 590,589 filed Feb. 3, 1984, now abandoned.

FIELD OF THE INVENTION

This invention relates to the filed of protein production using recombinant DNA biotechnology. In particular it relates to a process for preparing chymosin from an insoluble form of a chymosin precursor produced by a host organism transformed with a vector including a gene coding for the chymosin precursor.

BACKGROUND OF THE INVENTION

There are now numerous examples of commercially valuable proteins which may be produced in larger quantities by culturing a host organism capable or expressing heterologous genetic material. Once a protein has been produced by a host organism it is usually necessary to treat the host organism in some way, in order to obtain the desired protein in a free form. In some cases, such as in the production of the interferon in *E. coli* a lysis or permeabilisation treatment alone may be sufficient to afford satisfactory yields. However, some proteins are produced within a host organism in the form of insoluble protein aggregates which are not susceptible to extraction by lysis or permeabilisation treatment alone. It has been reported for instance that a human insulin fusion protein produced in *E. coli* forms insoluble protein aggregates (see D. C. Williams et al Science Vol. 215 pages 687–689). In the normal biologically active form (hereinafter referred to as the native form) a protein exists as a chain of amino acids linked by peptide bonds. The chain is folded into a thermodynamically preferred three dimensional structure, the conformation of which is maintained by relatively weak interatomic forces such as hydrogen bonding, hydrophobic interactions and charge interactions. A number of S—S covalent bonds may form intramolecular bridges in the polypeptide chain. The insoluble proteins produced by certain host organisms do not exhibit the functional activity of their natural counterparts and are therefore in general of little use as commercial production. The lack of functional activity may be due to a number of factors but it is likely that such proteins produced by transformed host organisms are formed in a conformation which differs from that of their native states. The altered three dimensional structure of such proteins not only leads to insolubility but also diminishes or abolishes the biological activity of the protein. It is not possible to predict whether a given protein expressed by a given host organism will be soluble or insoluble.

In our copending published British patent application GB2100737A (an identical disclosure of which is contained in assignee's U.S. application Ser. No. 389,063, filed Jun. 16, 1982, now abandoned) we described a process for the production of the proteolytic enzyme chymosin. The process involves cleaving one of the chymosin precursor polypeptides; preprochymosin, methionine-prochymosin or methionine-chymosin, which may be expressed from a host organism which has been transformed with a vector includes a gene coding for the relevant protein. The process for preparing a host organism transformed with a vector carrying a suitable gene is described in detail in the specification of our published British patent application GB2100737A and the same disclosure in our U.S. application Ser. No. 389,063, filed Jun. 16, 1982, now abandoned and the teachings thereof are incorporated herein by reference.

In the course of our work relating to the process of preparing chymosin we discovered that the chymosin precursor proteins produced by various host organisms used were not produced in their native form. In particular the methionine-prochymosin produced by *E. coli* is almost entirely produced as an insoluble aggregate and about 75% of the methionine-prochymosin produced in *Saccharomyces cerevisiae* is produced in an insoluble form.

In order to produce a chymosin precursor in a native form which may be cleaved to form active native chymosin the proteins produced by a host organism must be solubilised and converted into their native form before the standard techniques of protein purification and cleavage may be applied.

SUMMARY OF THE PRESENT INVENTION

According to the present invention we provide a process for production of chymosin in which an insoluble form of a chymosin precursor is produced by a host organism transformed with a vector including a gene coding for the chymosin precursor wherein the insoluble form of the chymosin precursor is solubilised to produce the soluble native form of the chymosin precursor prior to cleaving the soluble native form of the chymosin precursor to produce chymosin.

Preferably the insoluble form of the chymosin precursor produced by the host organism is preprochymosin or a fusion protein including the amino acid a sequence or preprochymosin, prochymosin or chymosin, for example, methionine-prochymosin or methionine-chymosin. Methionine-prochymosin is preferred as the chymosin precursors. The host organism may be a host organism or the progeny of a host organism which has been transformed (using the techniques described in our published British patent application GB2100737A) and the same disclosure in our U.S. application Ser. No. 389,063, filed Jun. 16, 1982 now abandoned with a vector including heterologous genetic material coding for the chymosin precursor. The host organism may be a yeast, for example, *Saccharomyces cerevisiae* or a bacterium, for example, *E. coli, B. subtilis, B. stearothermophilis,* or Pseudomonas. *Saccharomyces cerevisiae* or *E. coli* are the preferred host organisms.

The expression system comprising *E. coli* transformed with a vector including a gene coding for the chymosin precursor, methionine-prochymosin, is especially preferred.

The term 'insoluble' as used herein means in a form which, under substantially neutral conditions (for example pH in the range 5.5 to 8.5), is substantially insoluble is in insolubilised association with insoluble material produced on lysis of host organism cells. The insoluble product is either produced within the cells of the host organism in the form of insoluble relatively high molecular weight aggregates or may simply be associated with insoluble cell membrane material.

In order to produce the native form of the chymosin precursor it is necessary to alter the conformation of the insoluble product produced by the host organism. This may be done by denaturing the insoluble protein. Denaturing has the effect of abolishing the weak interatomic forces which maintain the protein in its three dimensional form causing the protein to unfold. The covalent bonds between adjacent atoms in the protein are left intact, including S—S bonds which maintain some of the three dimensional structure of the protein. The denatured state of a protein is less compact and is generally catalytically inactive. The denatured state is however usually soluble in the denaturing solution used. Removal of the denaturant from the solubilised proteins results in the refolding of the protein to produce the thermodynamically preferred native state of the protein. The renaturing is accompanied by the appearance of biological activity.

According to a preferred aspect of the invention the solubilisation involves reversibly denaturing the insoluble form of the chymosin precursor and subsequently allowing the chymosin precursor to renature, thereby producing the soluble native form of the chymosin precursor.

Preferably the insoluble form of the chymosin. precursor is denatured in an aqueous solution comprising urea at a concentration of at least 7M and the chymosin precursor is renatured subsequently by reducing the concentration of urea in the solution below a concentration effective to denature the chymosin precursor, to produce a soluble native form of the chymosin precursor.

When the insoluble chymosin precursor is treated with urea the insoluble precursor is completely solubilised. The disulphide intramolecular bridges of the protein are however preserved and subsequently act, as a nucleus for refolding. When the urea is removed, for example by dialysis, the protein returns to a thermodynamically stable conformation which, in the case of chymosin precursors, is a conformation capable of being converted to active chymosin by the methods described in published British patent application GB2100737A and the same disclosure in our U.S. application Ser. No. 389,063, filed Jun. 16, 1982 now abandoned. renatured proteins have the solubility characteristics of the native proteins.

In a further preferred aspect the insoluble form of the chymosin precursor is denatured in an aqueous solution comprising guanidine hydrochloride at a concentration of at least 6M and the chymosin precursor is renatured subsequently by reducing the concentration of guanidine hycrochloride in the solution below a concentration effective to denature the chymosin precursor, to produce a soluble native form of the chymosin precursor.

The physical effect of using guanidine hydrochloride is as discussed above for urea.

In a further preferred aspect the insoluble form of the chymosin precursor is denatured in an alkaline aqueous solution of between pH 9 and pH 11.5 and the chymosin precursor is renatured subsequently by reducing the pH of the solution below a pH effective to denature the chymosin precursor, to produce the soluble native form of the chymosin precursor. Preferably the alkaline aqueous solution is of pH between pH 10 and pH 11. Most preferred is an alkaline aqueous solution of pH from 10.5 to 10.9, preferably about 10.7.

Treatment of an insoluble chymosin precursor extract with an alkaline solution as described above does not result in complete solubilisation of the chymosin precursor. Since insoluble material such as cell debris is present at all times, a number of mass transfer effects are important. It has been found that multiple extractions with alkali are more efficient that a single extraction even when large extraction volumes are used. This also has the advantage of minimising the time for which the solubilised chymosin precursor is in contact with alkali. This is of importance since there is evidence that prochymosin slowly loses activity in alkaline solutions. Preferably, therefore, in this aspect of the invention the insoluble form of the chymosin precursor is present in conjunction with debris derived from the host organism which is insoluble in the aqueous solution and wherein one or more extractions of denatured chymosin precursor are performed. In view of the relatively low cost of the materials involved, the alkali solubilisation technique is attractive is terms of commercial exploitation.

The methods of solubilisation in a strong denaturant such as guanidine hydrochloride or urea and solubilisation using alkali, each solubilise significant percentages of the insoluble chymosin precursor which are found in extracts from host organisms. However, neither is quantitive in terms of recovery of native chymosin precursor. The reasons for this have not been clearly defined and are probably different for the two types of solubilisation. It appears that guanidine hydrochloride solubilities all the material present but only a portion is converted into proteins capable of activation to chymosin. Alkali treatment may not allow complete renaturation to form the native form of the chymosin precursor but in addition, does not solubilise all the insoluble form of the chymosin precursor. We have discovered that by combining the two methods a greatly enhanced recovery of chymosin precursor in its native state may be obtained.

According to a further preferred aspect of the present invention the insoluble form of the chymosin precursor is denatured in an aqueous solution, the resulting solution is diluted into 10 to 50 volumes of an alkaline aqueous solution of between pH 9 and pH 11.5 and the chymosin precursor is renatured by reducing the pH of the solution below a pH effective to denature the chymosin precursor, to produce the soluble native form of the chymosin precursor.

Preferably the solution containing the denatured chymosin precursor is diluted into an alkaline aqueous solution of pH between pH 10 and pH 11 and more preferably into an alkaline aqueous solution of pH from 10.5 to 10.9, preferably about 10.7.

The dilution introduces an element of physical separation between the denatured molecules, before renaturation is brought about, for example, by neutralisation of the alkaline denaturing solution. The dilution and resulting physical separation of the denatured molecules appears to assist their renaturation. The solubilisation process described immediately above leads to a recovery, in the case of methionine-prochymosin, of more than 30% compared to, for example, 10 to 20% for the multiple alkali extractions also described above.

Preferably, in the combined solubilisation process described above the insoluble form of the chymosin precursor is denatured in an aqueous solution comprising urea at a concentration of at least 7M or in a solution comprising guanidine hydrochloride at a concentration of at least 6M.

The present invention is preferably applied to the solubilisation of insoluble methionine-prochymosin produced by a host organism transformed with a vector including a gene coding for methionine-prochymosin. Preferably the host organism is *E. coli*.

A process for preparing host organisms coding for a number of chymosin precursors, including methionine-prochymosin, is described in detail in our published British patent application GB2100737A and the same disclosure in our U.S. application Ser. No. 389,063, filed Jun. 16, 1982 now abandoned. In addition published British patent application GB2100737A and the same disclosure in our U.S. application Ser. No. 389,063, filed Jun. 16, 1982 now abandoned contains details for producing active chymosin form a chymosin precursor prepared in its native form by the solubilisation process of the present invention.

Some embodiments of the present invention are now described in detail by way of Examples.

EXAMPLE 1

An experiment was conducted in which the solubilisation of insoluble methionine-prochymosin produced by *E. coli* cells transformed with vector pCT70 was achieved using urea or guanidine hydrochloride as denaturant. The preparation of the transformed *E. coli* cell line is described in detail in published British patent application GB2100737A and the same disclosure in our U.S. application Ser. No. 389,063, filed Jun. 16, 1982 now abandoned.

Frozen *E. coli*/pCT70 cells grown under induced conditions were suspended in three times their weight of 0.05M tris-HCl pH8, 1 mH EDTA, 0.233M NaCl, 10% glycerol (v/v) containing 130 $\mu$g/ml of lysozyme and the suspension was incubated at 4° for 20 minutes. Sodium deoxycholate was added to a final concentration of 0.05 and 10 $\mu$g of DNAase 1 (from bovine pancreas) was added per gram of *E. coli* starting material. The solution was incubated at 15° C. for 30 minutes by which time the viscosity of the solution had decreased markedly. An equal volume of a solution containing 0.01M tris pH 8, 0.1 mM EDTA, 5% glycerol was added and the extract centrifuged for 45 minutes at 4° C. and 10000$\times$g. At this stage effectively all the methionine-prochymosin product was in the pellet fraction, presumably as a result of aggregation or binding to cellular debris. The pellet was washed in 50 volumes of 0.01M tris. HCl, pH 8, 0.1M NaCl, 1 mM EDTA at 4°. After further centrifugation as above the supernatant solution was discarded and the pellet rapidly solubilised at room temperature in a buffer containing either 8M urea or 6M guanidine hydrochloride, 0.05M tris. HCl pH8, 1 mM EDTA and 0.1M NaCl. It was then dialysed overnight at 4° against 200 volumes of 0.01M tris. HCl pH8, 1 mM EDTA 0.1M NaCl and 10% glycerol. A heavy precipitate formed (insoluble E. coli proteins) which was removed by centrifugation to leave a solution of native methionine-prochymosin protein. The solution methionine-prochymosin was in a form which could be converted catalytically to active chymosin by acidification neutralization, substantially as described in published British patent application GB2100737A and the same disclosure in our U.S. application Ser. No. 389,063, filed Jun. 16, 1982 now abandoned.

EXAMPLE 2

An experiment was conducted in which the solubilisation of insoluble methionine-prochymosin produced by *E. coli* cells transformed with vector pCT70 was achieved using alkaline denaturation. The preparation of the transformed *E. coli* cell line is described in detail in published British patent application GB2100737A and the same disclosure in our U.S. application Ser. No. 389,063, filed Jun. 16, 1982 now abandoned.

Frozen *E. coli*/pCT 70 cells grown under induced conditions were suspended in three times their own weight of 0.05M Tris-HCl pH 8, 1 mM EDTA, 0.1M NaCl, containing 23 $\mu$g/ml PMSF and 130 $\mu$g/ml of lysozyme and the suspension was incubated at 4° C. for 20 minutes. Sodium deoxycholate was added to a final concentration of 0.5% and 10 $\mu$g of DNA ase 1 (from bovine pancreas) was added per gram of *E. coli* starting material. The solution was incubated at 15° C. for 30 minutes by which time the viscosity of the solution had decreased markedly. The extract, obtained as described above, was centrifuged for 45 minutes as 4° C. and 10000$\times$g. At this stage effectively all the methionine-prochymosin product was in the pellet fraction in insolublised form, presumably as a result of aggregation or binding to cellular debris. The pellet was washed in 3 volumes of 0.01M tris-HCl pH18, 0.1M NaCl, 1 mM EDTA at 4° C. After further centrifugation, as above, the supernatant solution was discarded and the pellet resuspended in 3 volumes of alkali extraction buffer: 0.05M $K_2$ $HPO_4$, 1 mM EDTA, 0.1M NaCl, pH 10.7 and the suspension adjusted to pH 10.7 with sodium hydroxide. The suspension was allowed to stand for at least 1 hour (and up to 16 hours) at 4° C., the pH of the supernatant adjusted to 8.0 by addition of concentrated HCl and centrifuged as above. Methionine-prochymosin, representing a substantial proportion of the methionine-prochymosin originally present in the pellet, was found to be present in the supernatant in a soluble form which could be converted to catalytically active chymosin by acidification/neutralisation activation treatment substantially as described in published British patent application GB2100737A and the same disclosure in our U.S. application Ser. No. 389,063, filed Jun. 16, 1982 now abandoned.

We further noted that re-extraction of the debris left after the first alkali extraction liberates an equivalent amount of prochymosin. Alkali extraction may be repeated to a total of 4–5 times with the liberation of approximately equivalent levels of prochymosin at each extraction.

EXAMPLE 3

An experiment was conducted in which the solubilisation of methionine-prochymosin produced by *E. coli* cells transformed with vector PCT70 was achieved using denaturation with guanidine hydrochloride, followed by dilution into an alkaline solution. The preparation of the transformed cell line is described in detail in published British patent application GB2100737A and the same disclosure in our U.S. application Ser. No. 389,063, filed Jun. 16, 1982 now abandoned.

E. coli/pCT70 cell debris containing insoluble methionine-prochymosin was prepared and washed as described in Example 1 above and the following manipulations were carried out at room temperature. The cell debris was dissolved in 3–5 volumes of buffer to final concentration of 6M guanidine HCl/0.05M Tris pH8, 1 mM EDTA, 0.01 m NaCl and allowed to stand for 30 mins–2 hrs. The mixture was diluted into 10–50 volumes of the above buffer at pH 10.7 lacking guanidine HCl. Dilution was effected by slow addition of the sample to the stirred diluent over a period of 10–30 minutes. The diluted mixture was readjusted to pH 10.7 by the addition of 1M NaOH and allowed to stand for 10 mins–2 hrs. The pH was then adjusted to 8 by the addition of 1N HCl and the mixture allowed to stand for a further 30 minutes before centrifuging as above to remove precipitated proteins. The supernatant so produced contained soluble methionine-prochymosin which could be converted to catalytically active chymosin by acidification and neutralisation and purified as described in published British patent application GB2100737A and the same disclosure in our U.S. application Ser. No. 389,063, filed Jun. 16 1982 now abandoned. In a very similar experiment an 8M urea buffer was used in place of the 6M guanidine HCl buffer described above. The results were as described above.

We claim:

1. In the process for the production of bovine chymosin comprising the steps of producing an insoluble aggregate form of the chymosin precursor preprochymosin, methionine-prochymosin or methionine-chymosin from a bacterial host cell transformed with a vector including a coding sequence for said chymosin precursor, solubilizing said insoluble aggregate form of said chymosin precursor to produce a soluble native form of said chymosin precursor to produce bovine chymosin, the improvement wherein said solubilizing is carried out by a combination of:
   1) denaturing said insoluble aggregate form of said chymosin precursor in an aqueous solution comprising urea at a concentration of at least 7M, and
   2) denaturing said insoluble aggregate form of said chymosin precursor in an aqueous solution of alkali hydroxide between pH 10 and pH 11.5, and, subsequent to steps (1) and (2), reducing the concentration of urea and reducing the pH of the solution below a pH effective to denature said chymosin precursor to produce the soluble native form thereof.

2. The process according to claim 1 wherein said chymosin precursor is reversibly denatured with said urea solution in step (1) and the solution resulting from step (1) is diluted into 10 to 50 volumes of said aqueous solution of alkali hydroxide in step (2).

3. Process according to claim 1 wherein steps (1) and (2) are carried out sequentially in numerical order.

4. Process according to claim 3 wherein the aqueous solution of alkali hydroxide has a pH between about 10.5 and 10.9.

5. Process according to claim 2 wherein said host cell is $E.\ coli$, and said aqueous solution of alkali hydroxide is sodium hydroxide in an alkali extraction buffer and has a pH between about 10 and 11.

6. A process according to claim 1 or 2 wherein the alkali is sodium hydroxide and wherein the pH of the aqueous solution of alkali is between pH 10 and pH 11.

7. Process according to claim 6 wherein the alkali hydroxide is sodium hydroxide in an alkali extraction buffer.

8. A process according to claim 1 or claim 2 wherein the insoluble aggregate form of the chymosin precursor is present in conjunction with debris derived from the host organism which is insoluble in the aqueous solution and wherein one or more denaturing steps of denatured chymosin precursor are performed.

9. A process according to claim 1 or 2 wherein the chymosin precursor is methionine-prochymosin.

10. A process according to claim 1 or 2 wherein the host cell is $E.\ coli$.

* * * * *

UNITED STATES PATENT AND TRADEMARK OFFICE
CERTIFICATE OF CORRECTION

PATENT NO. :   5,332,805
DATED      :   July 26, 1994
INVENTOR(S):   Carey et al.

It is certified that error appears in the above-identified patent and that said Letters Patent is hereby corrected as shown below:

Column 1, line 22, please delete "larger" and insert therefor --large--;

Column 1, line 62, please delete "described" and insert therefor --describe--;
Column 2, line 37, please delete the "a" after the word "acid";
Column 2, line 42, please delete "precursors" and insert therefor --precursor--;;
Column 3, line 42, please insert the word "The" before the word "renatured";

Column 4, line 16, please delete the second instance of "is" and insert therefor --in--;
Column 5, line 56, please delete "solution" and insert therefor --soluble--;

Signed and Sealed this

Twentieth Day of June, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,332,805

DATED : July 26, 1994

INVENTOR(S) : Carey et al.

It is certified that error appears in the above-identified patent and that said Letters Patent is hereby corrected as shown below:

On the title page, insert John S. Emtage, High Wycombe, England, as one of the inventors.

Signed and Sealed this

Tenth Day of October, 1995

Attest:

BRUCE LEHMAN

Attesting Officer

Commissioner of Patents and Trademarks